(12) United States Patent
Zhang et al.

(10) Patent No.: US 6,302,874 B1
(45) Date of Patent: Oct. 16, 2001

(54) METHOD AND APPARATUS FOR ELECTRICALLY ASSISTED TOPICAL DELIVERY OF AGENTS FOR COSMETIC APPLICATIONS

(75) Inventors: Lei Zhang; Gunter A. Hofmann, both of San Diego, CA (US)

(73) Assignee: Genetronics, Inc., San Diego, CA (US)

( * ) Notice: Subject to any disclaimer, the term of this patent is extended or adjusted under 35 U.S.C. 154(b) by 0 days.

(21) Appl. No.: 09/352,818

(22) Filed: Jul. 13, 1999

Related U.S. Application Data
(60) Provisional application No. 60/092,541, filed on Jul. 13, 1998.

(51) Int. Cl.[7] .................................................. A61M 31/00
(52) U.S. Cl. ............................................. 604/522; 604/501
(58) Field of Search .............................. 604/20–21, 500, 604/501, 522

(56) References Cited

U.S. PATENT DOCUMENTS

| | | |
|---|---|---|
| 3,163,166 * | 12/1964 | Brant et al. . |
| 4,262,672 | 4/1981 | Kief . |
| 4,474,570 * | 10/1984 | Arivra et al. . |
| 4,907,601 | 3/1990 | Frick . |
| 5,019,034 * | 5/1991 | Weaver et al. . |
| 5,042,975 * | 8/1991 | Chien et al. . |
| 5,058,605 | 10/1991 | Slovak . |
| 5,108,363 * | 4/1992 | Tuttle et al. . |
| 5,135,478 * | 8/1992 | Sibalis . |
| 5,215,088 | 6/1993 | Normann et al. . |
| 5,224,928 * | 7/1993 | Sibalis et al. . |
| 5,250,023 * | 10/1993 | Lee et al. . |
| 5,273,525 | 12/1993 | Hofmann . |
| 5,279,544 * | 1/1994 | Gross et al. . |
| 5,304,120 | 4/1994 | Crandell et al. . |
| 5,328,451 | 7/1994 | Davis et al. . |
| 5,358,483 * | 10/1994 | Sibalis . |
| 5,389,069 | 2/1995 | Weaver . |
| 5,425,752 | 6/1995 | Vu'Nguyen . |
| 5,439,440 | 8/1995 | Hofmann . |
| 5,445,611 * | 8/1995 | Eppstein et al. . |
| 5,464,386 * | 11/1995 | Hofmann . |
| 5,468,223 | 11/1995 | Mir . |
| 5,507,724 | 4/1996 | Hofmann et al. . |
| 5,507,802 | 4/1996 | Imran . |
| 5,536,267 | 7/1996 | Edwards et al. . |
| 5,547,467 | 8/1996 | Pliquett et al. . |
| 5,554,110 | 9/1996 | Edwards et al. . |
| 5,658,247 * | 8/1997 | Henley . |
| 5,667,491 | 9/1997 | Pliquett et al. . |
| 5,674,267 | 10/1997 | Mir et al. . |
| 5,702,359 | 12/1997 | Hofmann . |

(List continued on next page.)

FOREIGN PATENT DOCUMENTS

| | | |
|---|---|---|
| 863 111 | 1/1953 | (DE) . |
| 40 00 893 A1 | 10/1990 | (DE) . |
| 0 378 132 A2 | 1/1990 | (EP) . |
| 0 378 132 A3 | 1/1990 | (EP) . |

(List continued on next page.)

Primary Examiner—Mark Bockelman
(74) Attorney, Agent, or Firm—Gray Cary Ware Freidenrich; Lisa A. Haile (57) ABSTRACT

The present invention is based on the development of a method for cosmetic delivery of L-ascorbic acid-containing compositions to the layer of the skin wherein collagen formation takes place to enhance production of collagen and thereby combat some of the effects of aging and oxy-radical damage on skin. Sufficient electric pulses applied to a region of skin surface temporarily create new pathways through the lipid skin barrier, thereby delivering an L-ascorbic acid-containing composition through the lipid skin barrier and enhancing production of collagen in the region of the skin so treated. A handheld electrical pulser apparatus, optionally table-top adaptable, and methods of use for cosmetic treatment of degenerative skin conditions are provided by the invention.

54 Claims, 7 Drawing Sheets

U.S. PATENT DOCUMENTS

| | | |
|---|---|---|
| 5,718,702 | 2/1998 | Edwards . |
| 5,720,921 | 2/1998 | Meserol . |
| 5,749,847 | 5/1998 | Zewert et al. . |
| 5,780,052 | 7/1998 | Khaw et al. . |
| 5,786,454 | 7/1998 | Waksman et al. . |
| 5,789,213 | 8/1998 | Hui et al. . |
| 5,807,308 | 9/1998 | Edwards . |
| 5,807,309 | 9/1998 | Lundquist et al. . |
| 5,810,762 | 9/1998 | Hofmann . |
| 5,814,599 | 9/1998 | Mitragotri et al. . |
| 5,845,646 | 12/1998 | Lemelson . |
| 5,868,740 | 2/1999 | LeVeen et al. . |
| 5,869,326 | 2/1999 | Hofmann . |
| 5,873,849 | 2/1999 | Bernard . |
| 5,874,268 | 2/1999 | Meyer . |
| 5,879,891 | 3/1999 | Thompson . |
| 5,908,753 | 6/1999 | Kelly et al. . |
| 5,911,223 | 6/1999 | Weaver et al. . |
| 5,944,715 | 8/1999 | Goble et al. . |
| 5,964,726 | 10/1999 | Korenstein et al. . |
| 5,968,006 | 10/1999 | Hofmann . |
| 5,980,517 | 11/1999 | Gough . |
| 5,983,131 | 11/1999 | Weaver et al. . |
| 5,993,434 | 11/1999 | Dev et al. . |
| 5,994,127 | 11/1999 | Selden et al. . |
| 5,995,869 | 11/1999 | Cormier et al. . |
| 6,001,617 | 12/1999 | Raptis . |
| 6,002,961 | 12/1999 | Mitragotri et al. . |

FOREIGN PATENT DOCUMENTS

| | | |
|---|---|---|
| WO97/07826 | 3/1997 | (WO) . |
| WO99/44678 | 9/1999 | (WO) . |
| WO99/52424 | 10/1999 | (WO) . |

\* cited by examiner

METHOD AND APPARATUS FOR ELECTRICALLY ASSISTED TOPICAL DELIVERY OF AGENTS FOR COSMETIC APPLICATIONS

RELATED APPLICATION

This application relies for priority under 35 U.S.C. §119 (e)(1) on provisional application Ser. No. 60/092,541, filed Jul. 13, 1998.

FIELD OF THE INVENTION

The present invention generally relates to methods for enhancing the effectiveness of cosmetic pharmaceuticals used to improve the appearance of skin. In particular, the present invention relates to use of electroporation-mediated topical delivery of agents, such as Vitamin C.

BACKGROUND OF THE INVENTION

The main factors causing skin aging are natural processes (such as aging), lifestyle factors (such as smoking), and environmental stressors (such as UV radiation, chemical pollutants, etc.). It is now medically recognized that many of these factors damage skin through production of oxy-radical damage. Superoxide and the subsequently generated hydrogen peroxide and hydroxyl radical are oxygen-containing free radicals now known to be generated in vivo under a variety of normal and pathological conditions. An immense amount of work has been done in the last two decades documenting the deleterious behavior of oxygen radicals. These radicals have been implicated as causative agents for everything from sunburn to aging and have been shown to effect skin and other tissues by destroying lipid membranes, breaking down DNA, inactivating enzymes, and the like. As a result of this damage, certain anatomical changes occur, including thinning of the epidermis, thickening of the stratum corneum, reduction of blood supply to the skin, loss of collagen, and formation of age spots, lines and wrinkles.

L-ascorbic acid (vitamin C), a water-soluble antioxidant, can protect fatty tissues from oxy-radical damage by reacting with both superoxide and hydroxyl radicals. It also plays an integral role in collagen synthesis and wound healing by acting as a co-factor for hydroxylation of the proline and lysine residues of procollagen and promoting formation of the triple-helical conformation of mature collagen fibers. This conformation is required for the processing of procollagen to collagen (D. J. Prockop et al., "Intracellular steps in the biosynthesis of collagen" In: *Biochemistry of Collagen*, G. N. Ramachandran and A. H. Reddi (Eds.), Plenum Press, New York, 1976, 163–273; C. I. Levene and C. J. Bates, *Ann. NY Acad. Sci.* 258 [Suppl.]:288–306, 1975). L-ascorbic acid has also been shown to increase both the rate of transcription of procollagen genes and stability of procollagen mRNA (S. Tajima and S. R. Pinnell, Biochem. *Biophys. Res. Commun.* 106:632–637, 1982; B. L. Lyons and R. I. Schwarz, *Nucleic. Acids Res.* 12,2569–2579, 1984) as well as to modulate growth properties of cells (R. Hata et al., *Eur J Biochem.* 173:261–267, 1988).

In spite of these important activities of L-ascorbic acid for treatment of aging, environmental damage, wound healing, and the like, a drawback of its topical application is its instability. L-Ascorbic acid is chemically defined as an alpha-keto-lactone wherein the number 2 and 3 carbons are double-bonded and contain an acid-ionizable hydrogen in water (pK=4.2). Ascorbic acid is also a moderately strong reductant. These properties, which lead to instability in the ascorbic acid structure, are well known and have been burdensome to pharmacologists when attempting to formulate active ascorbic acid solutions. For example, at higher pH, ascorbic acid increasingly is transformed to the notoriously unstable ascorbate anion. This instability may be due to several causes, among which are the following:

a) Stereochemical strain due to polar repulsive forces. As a result, when the 2-hydroxy group ionizes, two negative charges form in close proximity, thereby favoring ring disruption.

b) Oxidative degradation due to the propensity of the ascorbate anion to act as a reductant. The one-electron oxidation product (dehydroascorbate free radical) tends to disproportionate, forming another ascorbate molecule and the two-electron oxidation product (dehydroascorbate), which is extremely unstable in aqueous solution and breaks down to ultimately form species such as L-threonic acid and oxalic acid. Transition metal ions can catalyze these reactions.

c) Degradation due to water attack. At lower ascorbic concentrations or ionic strength, water itself can react with and degrade the ascorbate molecule.

For these reasons, among others, scientists working in the field have had difficulty in formulating stable solutions of ascorbic acid which would be useful for cosmetic or dermatological needs. Nevertheless, because of the many beneficial pharmaceutical effects attributed to ascorbic acid, numerous attempts have been made to overcome these difficulties, as well as user compliance with the extended application schedule required, by adding minerals or metabolites and L-ascorbic acid derivatives into the formulation. Several commercial products are currently used in cosmetology such as C-Mate (L-ascorbic acid-2-P magnesium salt, neutral pH), Cellex-C™ (serum, pH 2.2), ESTER-CO (topical concentrate, pH 6.7), and products from Intaglio® (pH<3.5) and AGERA® (neutral pH). However, the required duration of therapy is relatively long (weeks to months) and skin irritation will occur with prolonged application of acidic pH formulations.

The cosmetic and therapeutic utility of topically applied Vitamin C and derivatives thereof, is also limited by the lipid-rich stratum corneum, thin layer of skin that acts as highly resistant lipid barrier to penetration of cosmetic agents into the skin. In both the pharmaceutical and cosmetic arenas, significant efforts have been put forth in attempts to overcome the skin's natural barrier to delivery of functional agents into the skin topically or into systemic circulation topically. Recent progress in skin drug delivery has been summarized in several review articles (M. R. Prausnitz, *Crit. Rev. Therap. Drug Carrier Syst.* 14(4):455–483, 1997; A. K. Banga (Ed.), *Electrically Assisted Transdermal and Topical Drug Delivery*, Taylor & Francis, Bristol, PA, 1998; A. K. Banga et al., *TIBTECH*, 16:408–412, 1998; G. Cevc, *Exp. Opin. Invest. Drugs* 6(12):1887–1937, 1997). Generally, three primary routes across the stratum corneum are available for molecular transport: (1) Normal or chemically modified skin allows diffusion of small molecules, usually following a tortuous intercellular path within the lipids of the stratum corneum. (2) Transcellular pathways crossing both the cells and intercellular lipids of the stratum corneum can be created by electroporation to allow passage of chemical compounds. (3) "Shunt" pathways through the hair follicles and sweat ducts may be utilized during iontophoresis (IPH), pressure-mediated delivery, and liposomal transport.

Electroporation is believed to involve the creation of new transient aqueous pathways (pores) in lipid bilayers by the application of a short electric pulse having a duration in the range from Usec to sec (D.C. Chang et al. (Eds.), *Guide to Electroporation and Electrofusion*, Academic Press, New York, 1992; J. C. Weaver, *J Cell. Biochem.* 51:426–435, 1993; J. A. Nickoloff (Ed.), *Methods in Molecular Biology*, Vols. 47, 48, 55, Humana Press, Totowa, N.J., 1995) and to drive molecules through the pores by electrophoresis (M. R. Prausnitz et al., *Proc. Nat. Acad. Sci.* 90.10504–10508, 1993; M. R. Prausnitz, *J. Control. Release* 40:321–326, 1996; M. R. Prausnitz et al., *J. Control. Release* 38:205–217, 1996; M. R. Prausnitz, et al., *Bio/Technology* 20:1205–1209, 1995; L. Zhang et al., *J. Bioelectrochem. Bioenerg.* 42.283–292, 1997. For a general discussion of EPT, see co-pending application Ser. No. 08/537,265, filed on Sep. 29, 1995, which is a continuation-in-part of application Ser. No. 08/467,566 filed on Jun. 6, 1995, which is a continuation-in-part of application Ser. No. 08/042,039 filed on Apr. 1, 1993 now abandoned, all of which are incorporated herein by reference.

Electrical studies have shown that short, high-voltage pulses can have dramatic and reversible effects on skin electrical properties. During a pulse, skin resistance drops as much as three orders of magnitude within microseconds. This alteration in skin resistance exhibits either complete or partial reversibility within minutes or longer. At relatively low voltages (<30 V), this drop of skin resistance can be attributed to electroporation of the appendages (e.g., sweat glands and hair follicles). At higher voltages (>30 V), EP of the lipid-comeocyte matrix leads to an additional drop of skin resistance Y. A. Chizmadzhev et al., *Biophys. J.* 74:843–856, 1998. Microscopic imaging suggests that up to 0.1% of skin area contributes to transport via transcellular and intercellular pathways (U. Pliquett et al., *Biophys. Chem.* 58:185–204, 1996; and M. R. Prausnitz et al., *J. Pharm. Sci.* 85:1363–1370, 1996).

Alternatives to topical delivery of L-ascorbic acid or its derivatives for skin improvement include chemical peels, dermabrasion, laser skin resurfacing, or continued large doses of L-ascorbic acid pills, each of which has a considerable discomfort associated with the treatment. For example, only a very small portion of L-ascorbic acid ingested penetrates into the skin and continuous large oral doses of L-ascorbic acid can cause gastrointestinal discomfort and diarrhea. Chemical peels, dermabrasion, and laser skin resurfacing generally involve a period of painful and unsightly healing of disrupted or burned skin surface layers.

Thus, there is a need in the art for new and better methods for enhanced topical delivery of L-ascorbic acid, derivatives thereof, or formulations containing L-ascorbic acid for skin improvement and dermatological purposes without adherence to an extended regimen and without substantial discomfort or skin irritation.

BRIEF DESCRIPTION OF THE INVENTION

The present invention overcomes many of the problems in the art by providing the discovery that penetration of L-ascorbic acid, or a cosmetically/pharmaceutically acceptable salt, ester or reducing derivative thereof, through the stratum corneum can be achieved without substantial pain or skin irritation by topically applying a composition containing such an active agent in conjunction with applying an electrical impulse to the region of skin. An invention method includes applying an electric pulse of a sufficient strength and duration to the a region of skin substantially contemporaneously with a composition comprising L-ascorbic acid, or a cosmetically/pharmaceutically acceptable salt, ester or reducing derivative thereof, to deliver an effective amount of the L-ascorbic acid or the derivative through the stratum corneum of the region of skin, thereby improving the condition of the region of skin without substantial pain or skin irritation. This invention has the potential to reduce the duration of skin rejuvenation as compared with conventional techniques.

In one embodiment, an effective amount of such a composition is introduced into a region of skin by substantially contemporaneously applying an electric pulse for cosmetically improving degenerative skin conditions in a subject in need thereof, for example by enhancing production of collagen in the region of skin and/or reducing therein the level of free oxygen radicals, and the like.

The invention methods are additionally advantageous when used in combination with other techniques (e.g., iontophoresis (IPH), vibration, phonophoresis, pharmacotherapeutics (optionally, liposome encapsulated)) as the combination can produce an additive or synergistic effect so that maximal cosmetic and/or therapeutic effects for improving skin appearance are produced. Among these techniques suitable for use in combination with electroporation as described herein, the one currently preferred is iontophoresis, a system for promoting topical absorption of a drug molecule through a skin barrier by generating an electric field between an anode and a cathode to cause a positively charged molecule to move from the anode to the cathode, or to cause a negatively charged molecule to move from the cathode to the anode (See *Journal of Controlled Release*, 18:213–220,1992; *Advanced Drug Delivery Review*, 9:119, 1992; *Pharmaceutical Research* 3:318–326, 1986).

In another embodiment the present invention provides methods for electroporation-enhanced dermatological delivery of L-ascorbic acid to a subject in need thereof. The invention dermatological delivery method comprises applying at least one electric pulse to the surface of a region of skin substantially contemporaneously with application thereto of a composition comprising ascorbic acid, or a cosmetically/pharmnaceutically acceptable salt, ester or reducing derivative thereof, said electric pulse having sufficient strength and duration to topically deliver an effective amount of the L-ascorbic acid or the derivative thereof to the region of skin. The invention dermatological delivery methods have both cosmetic and therapeutic applications.

BRIEF DESCRIPTION OF THE FIGURE

FIGS. 3A AND 3B are graphs showing distribution of electric fields across skin layers (from the surface of the stratum corneum to a depth of 2 mm in the dermis) under the conditions described in FIG. 2.

FIGS. 4A AND 4B are graphs showing distribution of electric fields at the depth of 250 $\mu$m below the skin surface under the conditions described in FIG. 2. The distance across the meander electrodes is represented along the X-axis.

FIGS. 5A through 5C are schematic drawings showing an invention handheld pulser.

FIGS. 6A through 6E are schematic drawings showing different configurations of disposable heads for use with the invention handheld pulsers.

FIG. 7 shows a meander electrode for use in the invention handheld pulser.

DETAILED DESCRIPTION OF THE INVENTION

In accordance with the present invention, there are provided methods for treating degenerative skin conditions in a subject in need thereof. The invention treatment methods comprise applying at least one electric pulse to the surface of a region of skin substantially contemporaneously with application thereto of a composition comprising L-ascorbic acid or a cosmetically/pharmaceutically acceptable salt, ester or reducing derivative thereof, said electric pulse having sufficient strength and duration to deliver an effective amount of the L-ascorbic acid, or a derivative thereof through the stratum corneum of the region of skin, thereby improving the condition of the region of skin without substantial pain or skin irritation. Generally the concentration of L-ascorbic acid or the derivative thereof in the L-ascorbic acid-containing composition is in the range from about 1% to 35% by volume, for example from about 20% to 33% by volume.

The invention cosmetic methods can be practiced upon any part of the body where a degenerative skin condition (i.e. aging) appears. In humans, the most commonly treated areas of the body are face, hand, arm, neck, chest, or leg. The term "degenerative skin conditions" is used broadly herein, and refers to such symptoms as flabby, sagging skin as well as wrinkles, age spots, actinic damage caused by UV radiation, and the like. Thus, degenerative skin conditions can result from either natural causes (such as aging), environmental causes (such as pollution and UV exposure), or such causes as poor diet. Disease conditions which inhibit endogenous production of collagen and/or oxy-radical scavengers, such as Vitamin C, or disrupt other natural processes that contribute to a healthy, more roseate, elastic skin can also contribute to degenerative skin conditions as the term is used herein. The term "treating" when used in reference to degenerative skin conditions further includes "preventing" or "inhibiting" formation of any of the above named symptoms of a degenerative skin condition. The invention dermatological treatment methods can also be used to promote healing of skin that has been damaged, either by trauma or by surgery.

As used herein, the term "a cosmetically/pharmaceutically acceptable salt, ester or reducing derivative of L-ascorbic acid" refers to forms of L-ascorbic acid that have been chemically modified to improve the stability and/or bioavailability of the L-ascorbic acid for topical administration, including specifically those modifications intended to reduce oxidation of L-ascorbic acid upon exposure to air and/or light, and those modifications intended to increase the solubility of L-ascorbic acid in lipids. For example, metal salts of L-ascorbic acid, such as sodium or phosphate salts, have increased stability in aqueous solutions at pH less than about 6.0. L-ascorbic acid 2-phosphate and sodium ascorbic acid are examples of metal salts of L-ascorbic acid. Modifications that increase the solubility of L-ascorbic acid in lipids include esterification, such as is found in the commercially available product Ester-C® or Agera®.

These and other such modifications are disclosed in, for example, Takashima et al, *Am. Perfumer & Cosmetics* 86:29, Jul. 1971 (esterifying the hydroxyl group to form ascorbic acid-3-phosphate and maintaining an alkaline pH), U.S. Pat. No. 2,400,171, which discloses stabilizing ascorbic acid by converting it to its calcium or zinc salt and preferably maintaining the pH at 7 to 7.3); and R. Hata et al., Seikagaku 58:823, 1986, which discloses a more stable phosphate derivative of L-ascorbic acid, L-ascorbic acid-2-phosphate that has been shown to act as a cofactor for collagen biosynthesis of cells in culture.

Additional components can also be added to the L-ascorbic acid-containing composition to aid in stabilizing the L-acorbic acid. For example, Ciminera and Wilcox, *J. Am. Pharm. Assoc. Sci. Ed.* 35: 363, 1946) disclose buffering an aqueous solution with an alkaline sodium salt), U.S. Pat. No. 4,367,157 discloses stabilizing an aqueous ascorbic acid solution by adding monothioglycerol and maintaining the pH between 4 and 7; U.S. Pat. No. 2,442,461 discloses stabilizing calcium ascorbate by adding an aliphatic thiocarboxylic acid and maintaining the pH between 5.2 and 5.6; U.S. Pat. No. 2,585,580 discloses stabilizing ascorbic acid with thio-sugars and maintaining the pH between 4.0 and 6.5.

The composition used in the invention methods may optionally comprise additional pharmaceutically-acceptable and cosmetically-acceptable safe active ingredients sufficiently high in purity and sufficiently low in toxicity to render them suitable for application to the skin of animals and humans. In addition, non-irritating carrier components as are known in the art can be used that are suitable for delivering the ascorbic acid to the skin. The components must be capable of being commingled with the ascorbic acid and the other ingredients in such a manner that there is no adverse interaction that would substantially reduce the efficacy of the composition during use. Accordingly, the compositions used in the invention methods may be formulated in a variety of forms suitable for topical administration, such as liquid (e.g., aqueous) suspensions or solutions, lotions, creams, sprays, sticks, ointments, pastes, and cosmetics.

The target for treatment of degenerative skin conditions or for cosmetic purposes, common referred to as "skin rejuvenation," is the epidermis. As used herein, the terms "topical delivery" or "topically introducing," and grammatical variations thereof, refer to the delivery of a composition into the skin, through/across the lipid bilayer or stratum corneum, or a combination thereof. An electric pulse that topically introduces a composition into the skin is believed to overcome the resistance of the skin barrier or alter the permeability of the lipid bilayer by substantial reduction in the electrical resistivity of the skin and/or creation of temporary hydrophilic windows in the lipid bilayer, which is also referred to herein as "breakdown" of the stratum corneum. This process is illustrated by computer simulation in Example 1 herein and in FIGS. 3A–B and FIGS. 4A–B. Thus, in a method of the invention in which an composition comprising L-ascorbic acid or a derivative thereof according to the invention is "topically or transdermally delivered" into the skin, the composition is driven into or through/across the skin. The "topically introduced" composition is likely driven across the stratum comeum into the underlying dermal layers, or into the blood supplying such tissue, by the electric pulse(s), to treat the skin tissue.

As used herein, the term "substantially contemporaneously" means that the electric pulse and the composition are applied to the region of skin to be treated reasonably close together in time. Preferably, the composition is administered prior to or concurrently with electropulsing. When applying multiple electrical impulses, the composition can be administered before or after each of the pulses, or at any time between the electrical pulses. When applying iontophoresis, vibration or ultrasound, the composition can be administered before or after each, and at any time between.

As used herein, the term "subject" refers to any animal. It is envisioned that the methods for topically delivering a composition comprising L-ascorbic acid, or a derivative thereof, described herein can be performed on any animal. Preferably, the subject is a human.

As used herein, the term "local," when used in reference to a composition, refers to its function in a particular region. Thus, an L-ascorbic acid-containing composition topically introduced into the skin is believed to exert its pharmaceutical or cosmetic activity function within the skin. Nevertheless, the skilled artisan will recognize that some topically introduced compositions may have a systemic effect or function, such that after topically introducing the composition into the skin, the composition is distributed to other areas of the subject thereby producing or contributing to treating degenerative skin conditions and/or promoting wound healing by acting at a site other than the skin. As used herein, the term "systemic," when used in reference to a composition, means that the composition functions outside the skin. It is specifically contemplated that compositions administered locally may function systemically as well.

In accordance with the invention methods an "effective amount" of an L-ascorbic acid-containing composition is delivered to a treated region of skin "topically," e.g., through the stratum corneum. An effective amount is an amount effective to produce a desired cosmetic and/or therapeutic effect, such as improving, preventing or inhibiting a degenerative skin condition or promoting skin healing in a subject in need thereof. In any event, an "effective amount" is generally a greater amount of the L-ascorbic acid or the derivative than will be delivered by passive absorption or diffusion, but should not be so large as to cause excessive adverse side effects, such as skin irritation, burning, cytotoxicity, or tissue damage. The amount required for cosmetic or therapeutic treatment will vary from subject to subject, depending on the type of formulation, the species, age, and general condition of the subject (physiological and psychological), the severity of the condition being treated (e.g., chronic vs. acute), the L-ascorbic acid-containing composition being employed, and the anatomical region of the skin being treated.

For example, the cytotoxicity ($MTT_{50}$, the amount of a substance required to kill 50% of the cells in cell culture) of ascorbate to fibroblasts appears to be at least partially dependent on the age of the subject. Tests of human dermal fibroblasts show that $MTT_{50}$ was 10,000 ppm for fibroblasts from a 26 year old and 2,500 ppm for fibroblasts from a 52 year old (at pH 7.5); However, when MAP (at pH 7.5) was tested as the active agent, $MTT_{50}$ was 75,000 ppm for fibroblasts derived from a 26 year old and higher than 100,000 ppm for a 52 year old (L. Fan et al., First World Congress for International Academy of Cosmetic Dermatology, Jan. 28–31, 1999, Malta, Italy). MAP exhibited significantly lower cytotoxicity in fibroblasts of all ages compared to L-acorbic acid. This data suggests caution when delivering very high concentrations of L-ascorbic acid or derivatives thereof to the epidermal/dermal junction, or deeper, on a sustained basis.

Thus, although it is not possible to specify an exact "effective amount," an appropriate "effective" amount in any individual case may be determined by one of ordinary skill in the art using the teachings herein. For example, using visual inspection to determine reduction in the number and/or depth of wrinkles, the amount and/or prominence of age spots, improvement in skin color (i.e., more roseate coloring) or overall improvement in the condition of skin, or by measuring certain skin parameters, the deterioration of which is associated with degenerative skin conditions, in response to various amounts of the composition, an effective amount can be readily determined. Such skin parameters may include an increase in skin elasticity, an increase in blood supply, a reduced level of free oxygen radicals or enhanced collagen production in the treated skin region as compared with a comparable untreated skin region. The amount can be adjusted by the individual or, in the event of any complication, by the physician.

The invention treatment method optionally further comprises further comprises additional steps that enhance the permeability of the stratum corneum of the skin, such as application of a permeation enhancers , microdermalabrasion, and the like. A "permeation enhancer" also can be included with electropulsing to increase topical introduction of a composition into the skin. As used herein, the term "permeation enhancer" refers to any action (e.g., mechanical, physical, chemical) or any composition that can increase or "augment" topically introducing a composition into the skin. The term "augment," when used herein as a modifier of topical introduction, means that the rate (over time) or amount of composition topically introduced into the skin via electropulsing is greater than that produced by electropulsing in the absence of the permeation enhancer. Thus, administering a permeation enhancer prior to, substantially contemporaneously with or after applying the L-ascorbic acid-containing composition to the skin may "augment" electrically induced topical introduction of the composition into the skin. Alternatively, a permeation enhancer can be mixed with the L-ascorbic acid-containing composition in the pharmaceutical formulation to be topically introduced. Permeation enhancer compositions that increase skin permeability include, for example, alcohols (e.g., methanol), alkyl methyl sulfoxides (e.g., DMSO), pyrrolidones (e.g., 2-pyrrolidone), surfactants, urea, glycerol monolaurate, polyethylene glycol monolaurate, glycerol monolaurate, docainehydrochloride, hydrocortisone, menthol, methyl salicylate, and the like. Permeation enhancers further include mechanical or physical actions that function in association with an electrical impulse (i.e., generally require applying an electrical pulse to augment topical introduction of the L-ascorbic acid-containing composition into the skin; e.g., vibration).

In another embodiment according to the present invention, there are provided methods for electroporation-enhanced dermatological delivery of L-ascorbic acid to a subject in need thereof. The invention dermatological delivery method comprises applying at least one electric pulse to the surface of a region of skin substantially contemporaneously with application thereto of a composition comprising L-ascorbic acid, a cosmetically/pharmaceutically acceptable salt, ester or reducing derivative thereof with the electric pulse having sufficient strength and duration to topically deliver an effective amount of the L-ascorbic acid or the derivative thereof to the region of skin. The invention dermatological delivery methods can be modified as described herein with reference to the various embodiments of the invention methods for treating degenerative skin conditions.

In another embodiment, the invention method further optionally comprises application of pressure to the skin surface after the L-ascorbic acid-containing composition has been topically applied to force the composition into pores and hair follicles in the skin. Pressure may be applied via the electrode during the treatment (to improve contact between the skin and electrode) or directly on the skin surface, thereby increasing topical introduction of a composition into the skin. Preferably, the pressure is applied in conjunction with a movement, such as a rubbing or stroking of the skin surface, for example, in a "back and forth" or circular motion. However, any convenient means for applying pressure to the skin surface can also be used, such as manual pressure via a cotton swab or gauze pad.

In another embodiment, the invention method optionally further comprises applying iontophoresis (IPH) in combination with an electrical impulse to topically introduce a greater amount of the composition into the skin than by pulsing alone, or that can drive the composition deeper into the skin, if desired, than by pulsing alone. A switching unit, such as an automated switch, optionally programmable, could be used to control the time between applying the impulse and applying IPH, as well as optionally controlling the time during which IPH is applied. Each parameter will be determined by the composition introduced, the desired effect, the concentration etc. The operation parameters can be set or programmed into the mini-generator.

In another embodiment, the invention method optionally further comprises applying vibration to the skin surface in combination with an electrical impulse to topically introduce a composition into the skin. For example, a phonophoresis unit can be used to aid in topically delivering a composition into the skin by means of ultrasound vibrations. Thus, by applying vibration or ultrasound before, after or during pulsing and/or iontophoresis on the region of skin surface being treated, the composition can be driven deeper into the skin or a greater amount of the composition can be driven into the skin than by pulsing alone. As above, a switching unit, such as an automated switch, optionally programmable, could be used to control the time between applying the impulse and applying vibration or ultrasound, as well as optionally controlling the time during which impulse, vibration or ultrasound is applied.

As used herein, the terms "impulse," "pulse," "electrical impulse," "electrical pulse," "electric pulse," "electropulse" and grammatical variations thereof are interchangeable and all refer to an electrical stimulus. Although the various terms are frequently used herein in the singular, the singular forms of the terms include multiple pulses. Preferred electrical impulses are pulsed electric fields applied via electroporation. The pulse can be unipolar, bipolar, exponential or square wave form.

The electric pulse can be provided by any electronic device that provides an appropriate electric pulse or electric source sufficient for topically introducing a composition into the skin. Suitable electric pulses for topically introducing compositions into the skin therefore include, for example, square wave pulses, exponential waves, unipolar oscillating wave forms, bipolar oscillating wave forms, other wave forms generating electric fields, or a combination of any of these forms. Each pulse wave form has particular advantages. For example, square wave form pulses provide increased efficiencies in transporting compounds into the cells in comparison to exponential decay wave form pulses, and the ease of optimization over a broad range of voltages, for example (Saunders, "Guide to Electroporation and Electrofusion," 1991, pp. 227–47). Preferably, the waveform used is an exponential or a square wave pulse.

An exemplary electric impulse for topically introducing a composition into the skin is a pulsed electric field, such as that provided by an electroporation apparatus. Exemplary pulse generators capable of generating a pulsed electric field include, for example, the ECM600, which can generate an exponential wave form, and the ElectroSquarePorator (T820), which can generate a square wave form, both of which are available from BTX, a division of Genetronics, Inc. (San Diego, Calif.). Additional electroporation type apparatus are commercially available and can be used to generate the pulse used in the invention methods. A pulse generator, physically connected to the electrode (as well as operationally connected) is preferably portable or lightweight and can optionally be powered by a portable DC power source, such as batteries, optionally being rechargeable.

Figure 1:
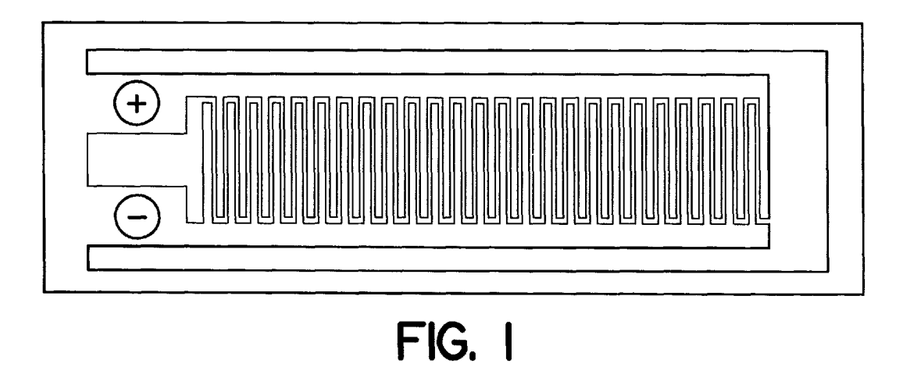
FIG. 1 is a photograph of a meander electrode that consists of an array of interweaving electrode fingers with alternating polarity. The width of electrode is 2 mm and the gap is 0.2 mm.

A typical electrical apparatus for use in practice of the invention methods will comprise a mini pulse generator in electrical connection with an electrode having a surface, such as a coating of plastic, suitable for application directly to skin. For electroporation through skin, the goal is an even distribution of an efficacious field. For topical delivery of active agents through skin, it is desirable to contain the electric field to a shallow skin surface layer so that the underlying nerves and muscles are not subjected to a strong electrical stimulation. After breakdown of the stratum corneum by electroporation, the depth of the electric field is related to the electrode spacing. A narrow spacing of multiple electrodes will confine the field to a surface region and, therefore is a preferred configuration. For example, depending on the formulation of the composition to be topically introduced, the electrode can be an insulated or porous meander electrode, which comprises an interweaving array of metal fingers coated on a thin film, such as plastic, for placement on skin. A typical meander electrode width is in the range of about 0.2 up to about1 mm, and an electrode gap of about 0.2 mm, wherein the gap can be filled with an electrically insulating substance), as shown in FIG. 1.

However, the nature of the electrode that can be used in the invention method(s) can be varied so long as it is capable of delivering a sufficient electric pulse as set forth herein. Thus, a variety of electrode types and configurations suitable for practice of the invention methods. For example, the electrode can be a wire electrode (useful for in vitro studies, and the like). Alternatively, the electrode can be a plurality of electrodes (e.g., a micropatch electrode as described in U.S. patent application Ser. No. 09/134,245, filed on Aug. 14, 1998, which is hereby incorporated herein in its entirety by reference). Alternatively, the electrode used in practice of the invention methods can be a porous electrode. The various electrodes used herein are preferably insulated to protect against excess heat or burning, current leakage, shock, etc. Appropriate electric pulsing parameters are set forth herein or can be determined using the teachings herein and, in view of these parameters, the skilled artisan can select among various suitable electrode types (e.g., ceramic, metal, etc.) and configurations (single wire, multiple wire, etc.) available in the art.

Generally, the pulse strength applied to the skin will range from about 25 to about 200 volts, preferably from about 25 to about 120 volts and more preferably from about 50 to about 80 volts. The pulse duration generally will be from about 10 microseconds ($\mu$sec) to 100 milliseconds (msec), for example, from about 500 $\mu$s to about 50 msec, or from about 2.0 ms to about 20 ms. There can be one or multiple pulses per cycle applied at spaced time intervals of about 0.1 msec to about 15 sec. Optionally, the number of pulses is from about 1 to about 30 pulses, for example, from about 1 to about 15 pulses per train. Generally, a train of about 5 to 15 pulse cycles are applied, and more than one such train of pulses can also be used.

Prior to use, the electrode is positioned so that contacts located on the outer surface are made with the mini generator, and the inner surface of the electrode is positioned to be in contact with the region of skin to be treated. Substantially contemporaneously, a desired composition is applied topically, to the region of skin to be treated, generally immediately before application of the electrode or while the electrode is being moved from one region to another on the skin surface. One or more appropriate electric pulses are then applied, preferably as a pulsed electric field.

A means for administering a composition can optionally be used in conjunction with performance of the invention method(s) to administer the composition to the region of skin prior to, substantially contemporaneously with, or after applying an electric pulse, iontophoresis, vibration or ultrasound. Depending on the specific formulation, a composition can be incorporated into a patch reservoir (e.g., similar to a nicotine patch), which is then attached both to the electrode and the skin surface. Formulations employed for IPH are advantageously used in this manner.

For human application, efficacy and sensation are the important criteria. The results of studies described herein in the Examples illustrate that there are at least four factors that influence these important considerations: formulation and its corresponding pH value, electrode design, electrical parameters, and skin site. For cosmeceuticals the preferred formulation is both stable and has a neutral pH. The stability of the formulation determines the period of time over which the L-ascorbic acid or derivative thereof will be active in the skin to accelerate procollagen processing to collagen and deposition of collagen in the cell layer. From the standpoint of patient comfort, the less irritation the product causes, the more acceptable it is. The studies described herein show that topical delivery of neutral or slightly basic compositions is enhanced to a greater degree than that of more acidic compositions (e.g., pH values<3.0), which are have a higher rate of passive diffusion. Therefore, electroporation as disclosed herein is particularly useful for enhancing topical delivery of L-ascorbic acid-containing compositions at pH values in the less irritating range from about 4.0–5.0.

In addition, the voltage, waveform type, pulse duration, capacitance, field strength and the number and timing of pulses applied without substantial pain or skin irritation will vary depending on the location of the region of skin treated and the formulation of the composition to be topically introduced. Tests conducted in a live human volunteer, described herein in Example 3, have shown that the face is more sensitive than the forearm, requiring use of a lower voltage and shorter pulses than for the forearm. In addition, the formulation of the L-ascorbic acid-containing composition should also be taken into account when determining the proper pulse parameters to be used to avoid substantial pain and/or skin irritation. For example, in these tests (Example 3) the tolerance limit for application of a single electric pulse to the human face was about 80 volts and a pulse duration of about 20 msec when the L-ascorbic acid-containing composition applied to the skin is formulated as a cream. By contrast, the level of tolerance for the human face drops to an electric pulse having a voltage of no more than about 50 volts and a duration of no more than about 2 msec when the L-ascorbic acid-containing composition is formulated as an aqueous suspension or solution. For the forearm, relatively higher voltages and longer pulses are tolerable. For example, testing of the human volunteer showed that the level of tolerance for application of a single pulse to the forearm was at about 70 volts for a pulse duration of about 10 msec when the L-ascorbic acid-containing composition formulated as an aqueous suspension.

Particular electrical parameters for topically introducing a composition into the skin, other than those exemplified herein, can be empirically determined if necessary, in view of the teachings herein and of the general knowledge of those having skill in the art, for example, relating to the electroporation of mammalian cells in vivo.

In accordance with another embodiment of the present invention there is provided a handheld pulser for applying electric pulses of sufficient time and duration to cause one or more of electroporation, iontophoresis or electroincorporation. In one aspect of the invention, the pulser comprises a support member, and an electrode having an optional electrically conductive cover (See FIG. 5A), wherein the support member is of a size and shape to be handheld, and wherein the electrode is attached to the support member and is operatively connected to a pulse generator. The pulser may optionally have a controlling means for switching the pulse generator on and off.

As used herein, "support member" means a rigid body of the kind associated with, for example, a handheld electric shaver, or the like. Accordingly, the support member may be constructed of any suitable material such as plastic, or the like.

Figure 7:
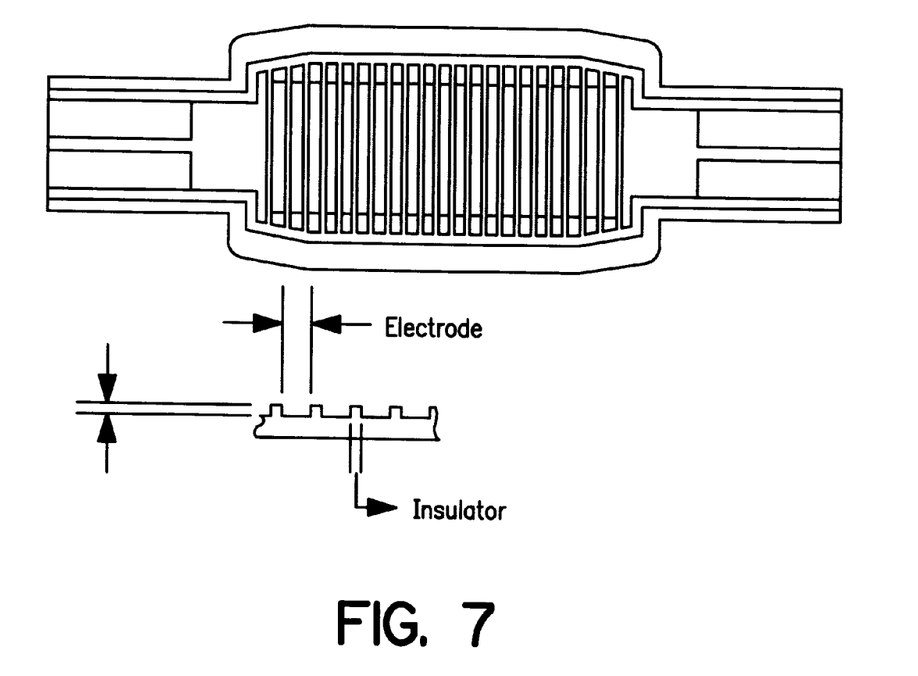
FIG. 7 shows a top view of the meander electrode as well as a side view the same meander electrode, with the width of an individual electrode indicated by double arrows.

As used herein, "electrode" means any electrode that can be adapted for use in the pulser so long as it is capable of delivering a sufficient electric pulse as set forth herein. Thus, a variety of electrode types and configurations are contemplated in the invention apparatus. For example, the electrode can be an insulated or porous meander electrode, having an interweaving array of metal fingers coated on a thin film, such as plastic, which can be placed on skin, as is illustrated herein in FIGS. 7A–B. In another embodiment, the electrode is a plurality of electrodes (e.g., a micropatch electrode as described in U.S. patent application Ser. No. 09/134,245, filed on Aug. 14, 1998, which is hereby incorporated herein in its entirety by reference). The various electrodes used herein are preferably insulated to protect against excess heat or burning, current leakage, shock, etc. Appropriate electric pulsing parameters are set forth herein or can be determined using the teachings herein and, in view of these parameters, the skilled artisan can select among various suitable electrode types (e.g., ceramic, metal, etc.) and configurations (single wire, multiple wire, etc.) available in the art.

Figure 5A:
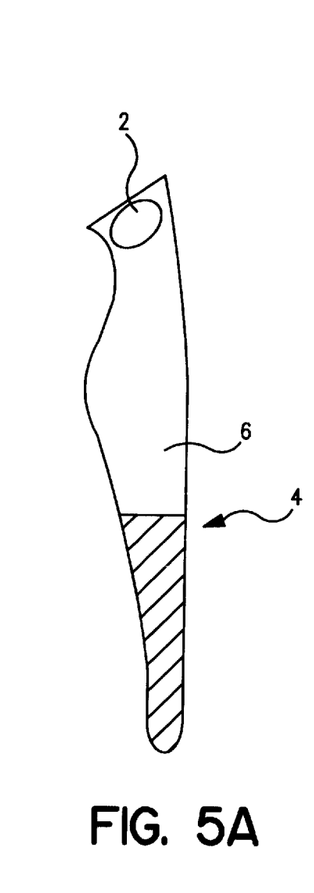
FIG. 5A is a side view showing an adapter hole for a disposable head and FIG. 5B is a frontal view.
Figure 5B:
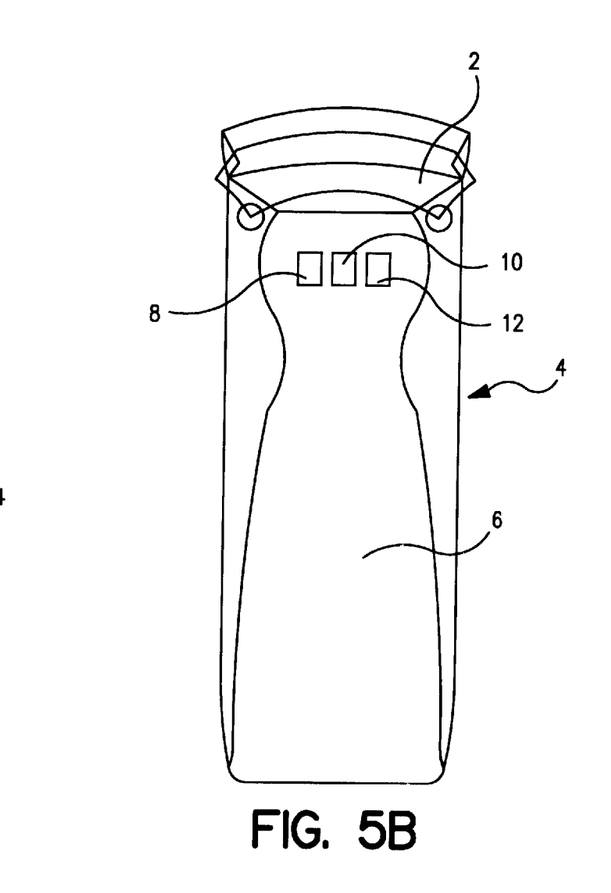

As shown in FIGS. 5A–B, it is presently contemplated that the electrode portion 2 of the pulser 4 be attached to one end of the support member 6. Again, using the standard electric shaver as an analogy, the electrode would be similarly located as the blades of the shaver. Of course any convenient location of the electrode can be employed in the practice of the present invention.

Invention pulsers may be used by lay people or professionals. Accordingly, it is contemplated that invention pulsers can have user adjustable options of varying degrees of sophistication. Accordingly, as shown in FIG. 5B, the invention apparatus can have a variety of functionalities in addition to the optional controlling means 8 ("switch button") for applying an electric pulse. For example, the apparatus can have an indicating means 10 and 12, which can be selected to indicate such parameters as "apparatus ready," the various pulse parameter settings (e.g., voltage, capacitance, pulse duration, time delay between pulses, pulse wave type), pulse(s) applied, parameters of the applied pulse(s) (e.g., voltage, capacitance, pulse duration, pulse wave type, number of pulses) or a combination thereof. In addition to visible displays as shown in FIG. 5B, indicating means can be audible, or a combination of visible and audible. For example, a single audible "beep" can indicate that the "apparatus is ready," two audible "beeps" can indicate that a pulse has been correctly applied and three audible "beeps" can indicate a malfunction or that the pulse was not or was improperly applied. Visual indicating means include analog or digital alpha-numeric displays (e.g., LCD, LED and the like), as in watches, and further can include illuminating means for low light visualization, for example, by white light, electroluminescent backlighting for LCD or electroluminescent lamps (i.e. INDIGLO™), or by various fluorescent or radioactive illuminating compositions, and the like.

Figure 5C:
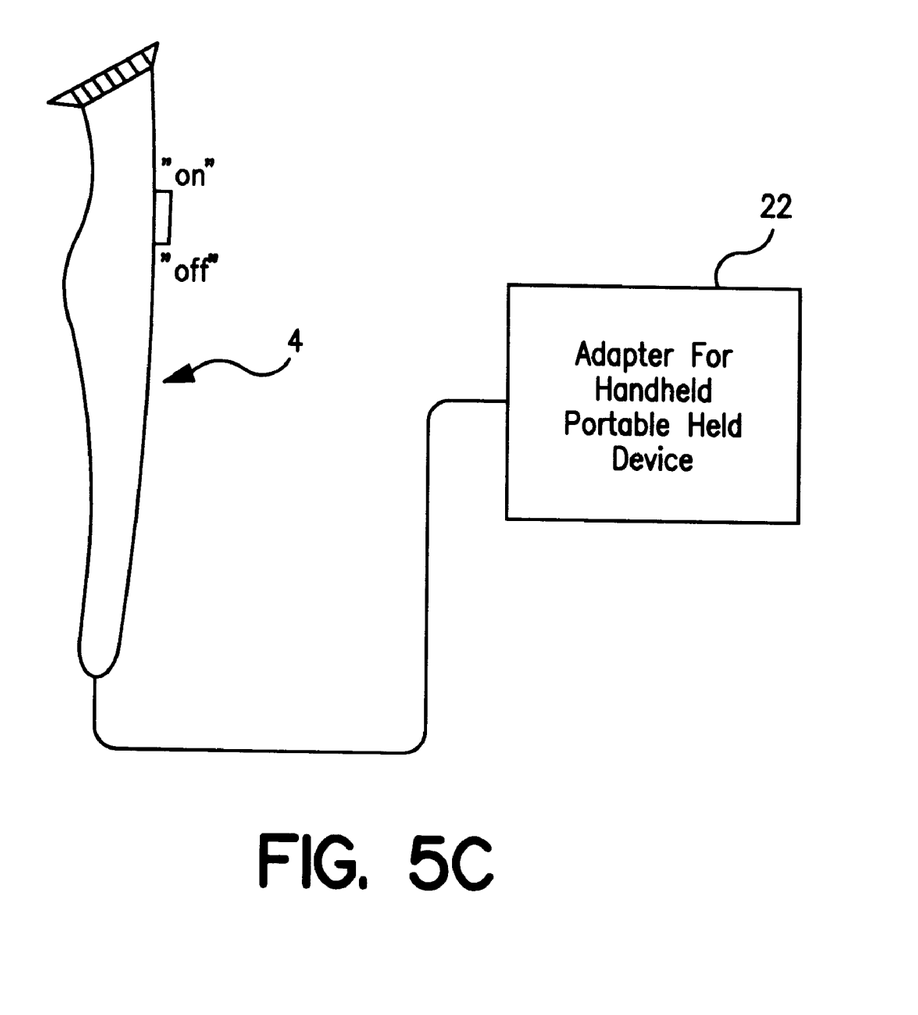
FIG. 5C is a schematic drawing showing an adapter for fastening the handheld pulser to a stationary surface, such as a table top.

As shown in FIG. 5C, the invention pulser may optionally be fitted with an adapter 22 for fastening the handheld pulser to a stationary surface, such as a table top.

Additional "user friendly" functions include the aforementioned controlling means for applying an electric pulse (e.g., pushbutton, knob, lever switch, dial and the like) as well as means for adjusting parameters (e.g., pushbutton, knob, lever switch, dial and the like) including, for example, pulse duration, voltage, capacitance, field strength, number, and wave type. Means for adjusting, setting, storing or retrieving one or more pulse parameters also are included herein. Such means include traditional mechanical electronic controls (e.g., a selector switch controlling each parameter in which the switch has a plurality of settings; as well as a chip control (e.g., silicon wafer types commonly used in the computer industry) which is controlled, for example, by a pushbutton interface, as in watches for example. A chip, optionally removable from the apparatus or, user and/or manufacturer programmable for control of the various pulse parameters set forth herein also is contemplated. Storage capacity of such a chip is sufficient to provide virtually unlimited fine control of the various parameters, as well as storing different pulse parameter settings for different compositions, users and the like. As each of the various electronic functionalities of the invention apparatus described herein can be controlled or managed by a computer chip, a chip affords the option of additionally incorporating software, if desired, said software optionally user programmable.

Depending on the formulation of the therapeutic agent to be introduced into the skin and the condition of the skin, it may be advantageous to apply one or more additional treatment modalities to facilitate the introduction of the therapeutic agent. Such additional modalities may include vibration, phonophoresis, and the like. Accordingly in another aspect of the present invention, a vibration unit also can optionally be included in the apparatus, which can be used in combination with an electrical impulse to introduce a composition into the skin. A phonophoresis unit, which can transdermally introduce a composition into the skin by means of ultrasound, also can optionally be included in the apparatus, if desired. Thus, by applying vibration or ultrasound before, after or during pulsing and/or iontophoresis on the skin, the composition can be driven deeper into the skin or a greater amount of the composition can be driven into the skin than by pulsing alone. As above, a switching unit, such as an automated switch, optionally programmable, could be used to control the time between applying the impulse and applying vibration or ultrasound, as well as optionally controlling the time during which impulse, vibration or ultrasound is applied.

A means for administering a composition can optionally be included in the electrical apparatus, which can be used to administer the composition to the skin prior to, substantially contemporaneously with, or after applying an electric pulse, iontophoresis, vibration or ultrasound, in their various embodiments. Depending on the specific formulation, a composition can be incorporated into a patch reservoir (e.g., as a nicotine patch), which is then attached both to the electrode and the skin.

Invention apparatus is adaptable to a number of topical application needs, and is similarly adaptable to a number of different body surfaces. Accordingly, in one embodiment of the present invention, the electrode is detachable, thereby allowing different electrode types and/or shapes to be employed. In a particular aspect of the present invention, the electrode can be attached to the support unit by a variety of suitable means known to those of skill in the art. For example, the electrode can be directly attachable to the support means by a mechanical attachment (e.g., clips, or the like). In another aspect of the present invention, the electrode may be attached to a mounting bracket which is, in turn, attachable to the support unit. Electrodes may be mounted to the detachable mounting bracket by means of an integral adhesive means (such as an adhesive strip, as shown for example in FIG. 6B, or the like).

As used herein, "mounting bracket" means a device fabricated from any suitable material for mounting an electrode thereto. Depending on how current is to be conveyed from the pulse generator to the electrode, suitable materials can be non-conductive (e.g., plastics, polymer resins, or the like), or conductive (e.g., metal, metal alloy, or the like).

Mounting brackets, like electrodes can have a variety of shapes to accommodate the different body surfaces encountered in use. Accordingly, as depicted in FIGS. 6A–E, the electrode or mounting bracket can be square, round, crescent (or moon-shaped), tubular, or the like. The tube shape is particularly useful when employed in conjunction with an axle running through its longitudinal axis, as shown in FIG. 6E. In this manner, the electrode can be rolled along the skin surface rather than being slid along the skin surface as with a static electrode. Contact regements located along the side of the roller will dispense the treatment fluids while the roller turns. This may be of particular advantage when treating delicate skin or when abrasion is otherwise a concern. Of course, there are means known to those of skill in the art for reducing the friction between a static (i.e., non-rolling) electrode and the skin. Reduced friction surfaces may be employed so long a the surface material allows pulse transmission to the skin.

Figure 6A:
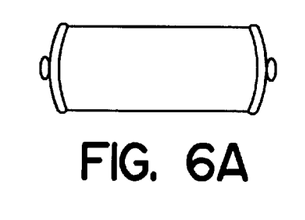
FIG. 6A shows the top view and FIG. 6B shows a side view of a square type head with clips to attach the head to the body of the pulser.
Figure 6B:
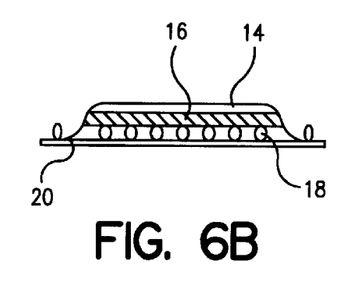
Figure 6C:
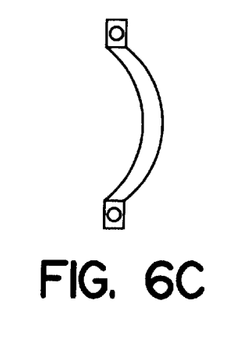
FIG. 6C shows a top view of a moon type head.
Figure 6D:
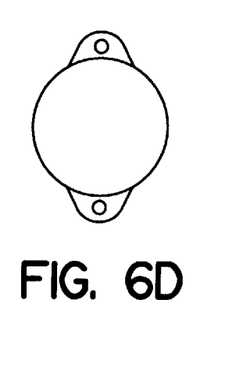
FIG. 6D shows a top view of a round type head.
Figure 6E:
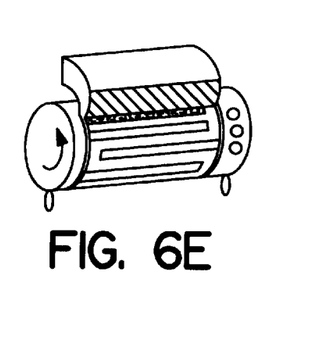
FIG. 6E shows a perspective view of a roller type head.

Alternatively, as shown in FIG. 6B, an electrode cover 14, for example made of an elastic material, and a cosmetic reservoir 16 can be placed atop the electrode 18, and the electrode 18 can be backed with an adhesive film 20 that can be peeled off for use.

The optional electrode cover can be manufactured of essentially any material compatible with applying an electrical impulse to the skin. The electrode cover can be made of a single material type or can be made of multiple material types. In one embodiment, the electrode cover is manufactured of a single flexible cushioned or compressible material, e.g., elastic-containing cotton, or the like, as shown, for example in FIG. 5. Preferably, the various electrode cover embodiments of the invention apparatus are hypo-allergenic, non-allergenic or so modified to be non-allergenic.

It may be desirable to couple a dispensing unit to the handheld pulser. In this aspect of the present invention, the pulser has a unit attached thereto for containing and dispensing the agent to be applied to the skin. The dispensing unit may optionally be controllable to dispense a measured amount of agent. The dispensing unit can be any device compatible with the electronic pulse to be delivered by the pulser, and is contemplated to include passive devices such as, for example, a reservoir-type patch or sponge; and active devices such as a pump or even an injection means, such as a syringe, or the like.

In addition to efficacy, both sensation and user safety are important. Thus, in another embodiment, the invention further provides an apparatus having means for preventing applying excess pulse voltage, duration, field strength and/or number. Any means which passively or actively interrupts or disrupts the electric circuit, including fuses, circuit breaker switches, and the like, or devices that actively monitor the various pulse parameters and interrupt or disrupt the electric circuit to prevent excess pulse voltage, duration, field strength, pulse number from being applied can be incorporated into the circuit path. Those skilled in the art of electrical devices will know of other protective elements that prevent applying excess pulse voltage, duration, field strength or number.

The electric pulse can be provided by any electronic device that provides an appropriate electric pulse or electric source sufficient for introducing a topically applied composition into the skin. Suitable electric pulses for transdermally topically applied composition into the skin therefore include, for example, square wave pulses, exponential waves, unipolar oscillating wave forms, bipolar oscillating wave forms, other wave forms generating electric fields, or a combination of any of these forms. Each pulse wave form has particular advantages; square wave form pulses provide increased efficiencies in transporting compounds into the cells in comparison to exponential decay wave form pulses, and the ease of optimization over a broad range of voltages, for example (Saunders, "Guide to Electroporation and Electrofusion," 1991, pp. 227–47). Preferably, the waveform used is an exponential or a square wave, or bipolar oscillating wave forms.

An exemplary electric impulse for introducing a topically applied composition into the skin is a pulsed electric field, such as that provided by an electroporation apparatus. Because the apparatus of the present invention is designed to be handheld, it is presently preferred that the pulse generator be integrated into the support member. Power to the pulse generator can be supplied by any suitable means, including disposable battery, rechargeable battery, household AC current, or the like. Alternatively, the pulse generator may be a "table top" unit, wherein the pulse is transmitted to the handheld pulser via conducting wire, or the like. Exemplary pulse generators capable of generating a pulsed electric field include, for example, the ECM600, which can generate an exponential wave form, and the ElectroSquarePorator (T820), which can generate a square wave form, both of which are available from BTX, a division of Genetronics, Inc. (San Diego, Calif.). Additional electroporation type apparatus are commercially available and can be used to generate the pulse for the invention apparatus and in practicing the invention methods. Such pulse generators can be operatively connected to the pulse applicator, or alternatively can be physically contained within the pulse applicator. A pulse generator, physically connected, is preferably portable or lightweight, and an optional portable DC power source, such as batteries, optionally being rechargeable, can be included to provide the power source to the pulse generator.

The following examples are intended to illustrate but not limit the invention. While they are typical of those that might be used, other procedures and applications of the invention methods known to those skilled in the art may alternatively be used.

EXAMPLE 1
Computer simulation

For computer simulations, the skin structure was reduced to a biophysical model wherein a very thin (typically 15–30 $\mu$m), highly resisitive layer, representing the SC, covers a thicker, highly conductive layer, representing the epidermis and dermis. Field plots (V/cm) were used in order to get a better understanding of fields generated by meander type electrodes in human skin The objective was to solve Laplace's equation for electrostatic potential, ($\overline{\nabla}^2 V = 0$, and then find a solution for field strength from the equation $E = -\overline{\nabla} V$ throughout the electrostatic environment. EMP software (Field Precision, New Mexico) was used for this purpose, and data was obtained to import into the plotting programs, as follows.

Figure 3A:
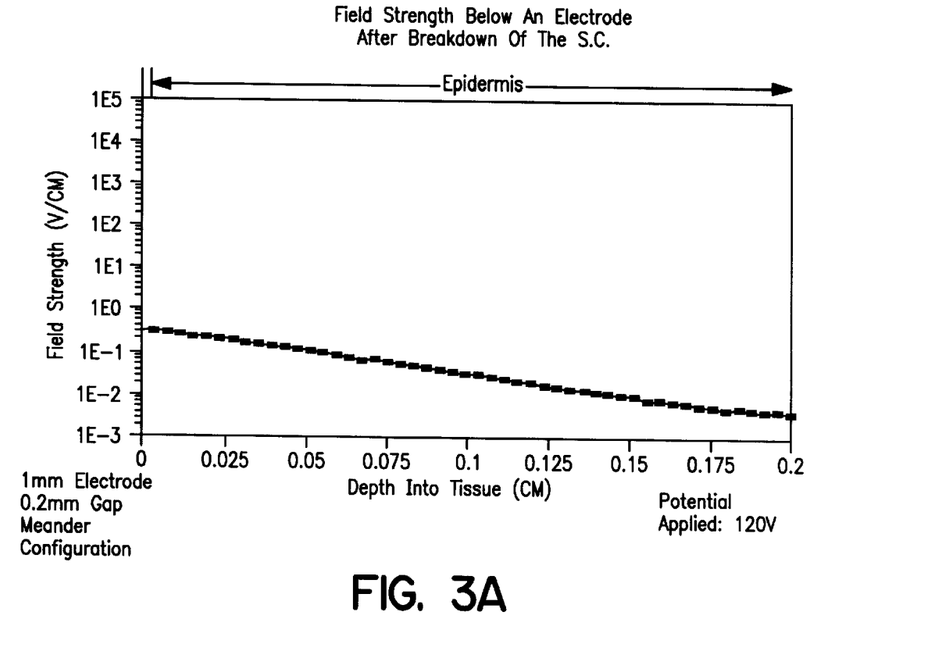
FIG. 3A shows the electric field distribution before breakdown of the stratum corneum by electroporation.

The simulation model contained a meander electrode comprised of six individual electrodes of alternating polarity, each electrode being 1 mm wide, with a 0.2 mm space between adjacent electrodes, as illustrated in FIG. 1. The simulation further included immersion of the electrodes in a saline solution that had a resistivity of 1 kohm-cm and placement of the electrode approximately 10 $\mu$m above the stratum corneum. In the first run of simulation, the stratum corneum was selected to have a thickness of 15 $\mu$m with a resistivity of $6.0 \times 10^5$ kohm-cm. The underlying epidermis and dermis was selected to have a thickness of 2 mm with a resistivity of 5 kohm-cm. Specific surface resistivities were calculated by the model and these numbers were divided by their respective skin layer thicknesses. The potential applied was 120 V. A graph showing the simulated field strength below a single electrode in the meander electrode with tissue depth (from zero to 0.2 cm) before breakdown of the stratum corneum is shown in FIG. 3A.

Figure 3B:
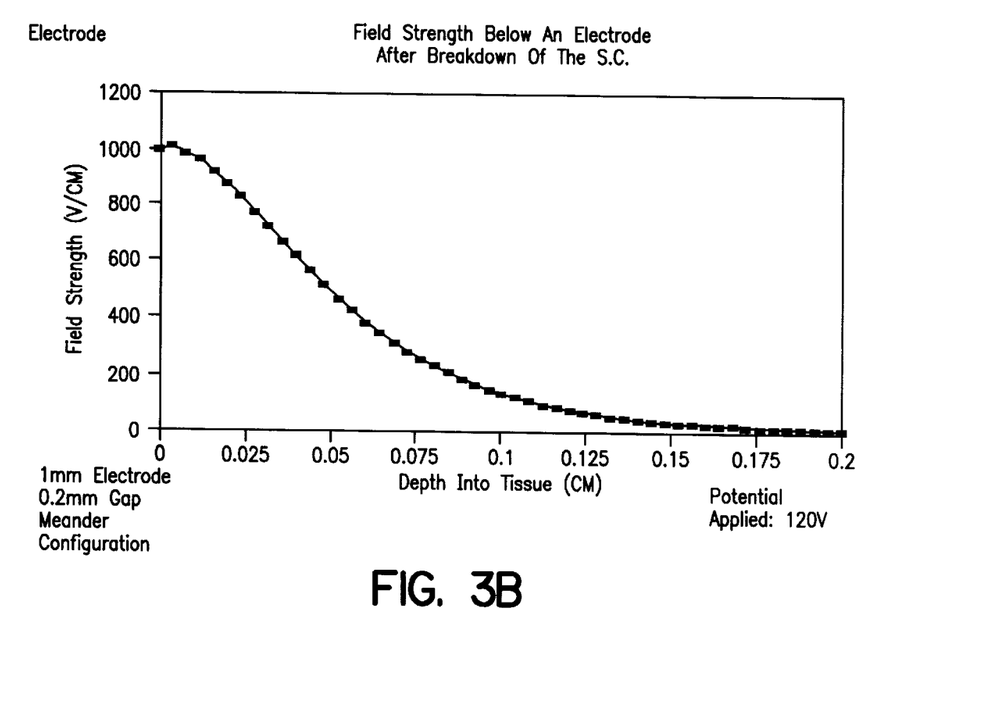
FIG. 3B shows the electric field distribution after breakdown of the stratum corneum. The depth of the stratum corneum is indicated by a pair of narrow black bars on the upper left corner next to the epidermis.

A second run of simulation was performed as in the first run, except that the resistivity of the stratum corneum was made equivalent to the resistivity of the epidermis to simulate the breakdown of the stratum corneum as would happen if transient aqueous pathways or pores in the lipid bilayers were created. The potential applied was again 120 V. Finally, the distribution of electric fields at different depths of the skin was calculated using the model for a time t=0, before the breakdown of the SC, and also for a time t>0 after the breakdown of the stratum corneum. FIG. 3B is a graph showing the simulated field strength below a single electrode in the meander electrode at a range of tissue depth from zero to 0.2 cm with skin resistivity reduced to simulate the breakdown of the stratum comeum.

Figure 4A:
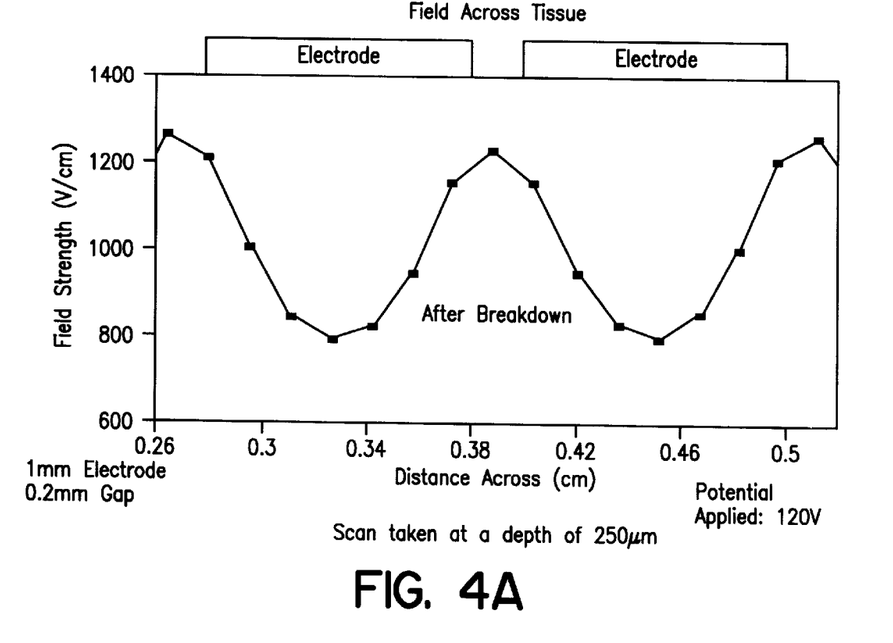
FIG. 4A shows the distribution of electric fields before breakdown of the stratum corneum by electroporation and FIG. 4B shows the distribution after breakdown of the stratum corneum.
Figure 4B:
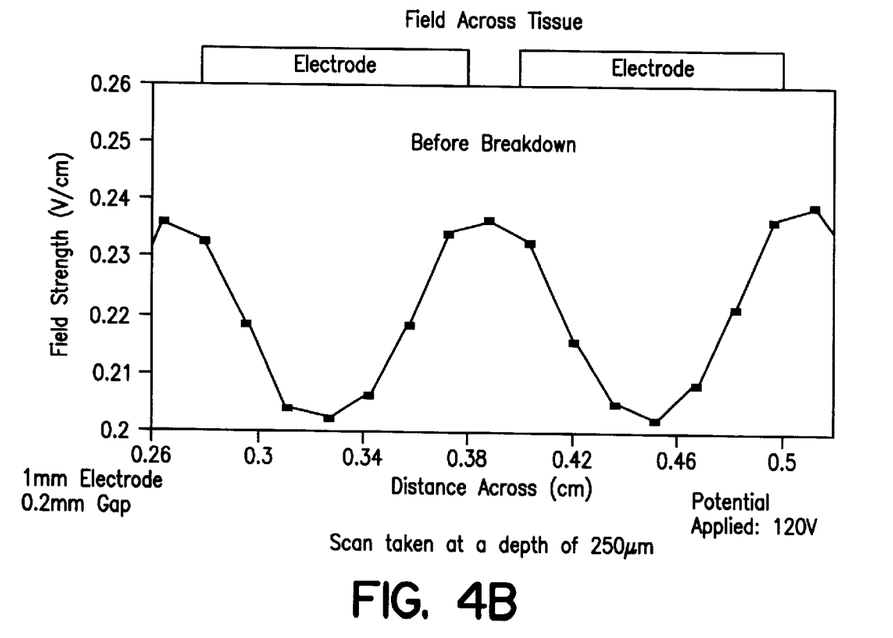

The results of these calculations show that before breakdown of the stratum corneum (FIG. 3A), the field strength in the stratum corneum was five orders of magnitude higher than in the epidermis (<0.2 V cm$^{-1}$). After breakdown of the stratum corneum, the field strength increased by four orders of magnitude within the epidermis region at a skin depth of 125 μm (FIG. 3B). Interestingly enough, the increase of field strength always occurred around the edge of the electrodes (FIGS. 4A and 4B). The area below the center of each electrode had the lowest field.

Figure 2:
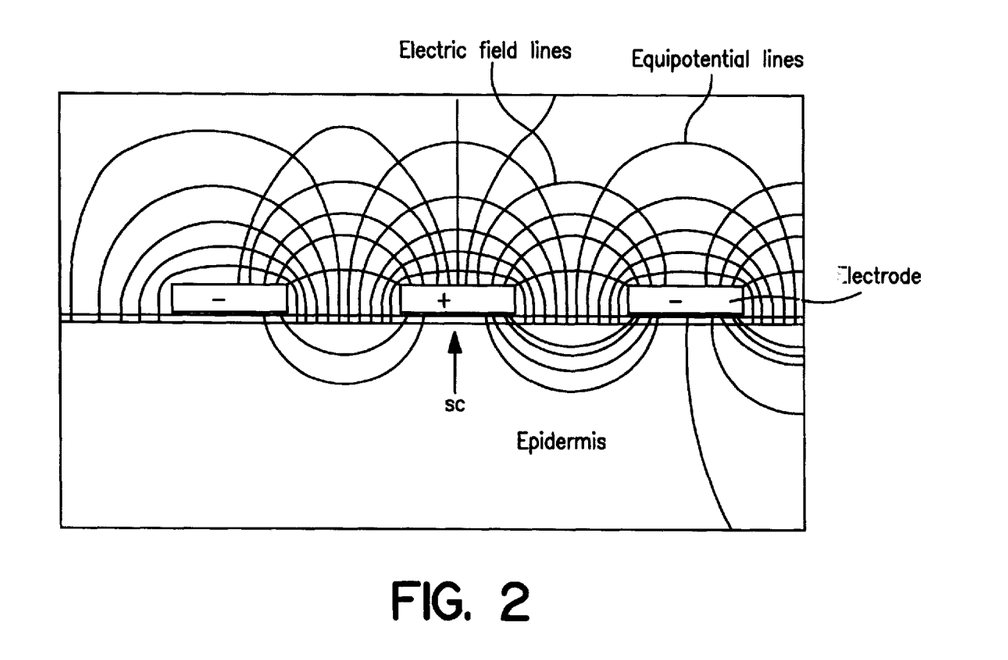
FIG. 2 is a simulation plot of equipotential and electrostatic field lines generated by the meander electrode of FIG. 1 at a depth 10 $\mu$m above the stratum corneum upon application of an electric potential of 120 volts to the skin surface.

The field strength data was also obtained from the simulation model across the skin surface for a width (0.26 cm to <0.5 cm) greater than the width of two electrodes in the meander electrode to determine the relationship between distance from the electrode and the field strength generated in skin at a constant depth of 250 μm. The results of these calculations, shown in FIG. 2, indicate that the potential drop between the electrodes in the meander electrode is mainly confined to the stratum corneum.

EXAMPLE 2
In vitro electroporation-assisted delivery of L-Ascorbic acid

In vitro delivery studies were conducted to determine the relative efficacy of two L-ascorbic acid formulations, one in cream formulation and one having crystals of L-ascorbic acid in solution. For the cream formulation, Intaglio® cream( (pH 3.5, Research Institute for Plastic, Cosmetic and Reconstructive Surgery, Inc., S.D.) was used, which contains 20% L-ascorbic acid. This cream formulation has been used in physicians' offices for skin resurfacing. For the aqueous suspension formulation, 2 g of L-ascorbic acid crystals were suspended in a vial containing 6 ml of distilled water at room temperature (pH 1.86). The vial containing the suspension was wrapped with aluminum paper and was kept in a cold water bath during experiments to prevent oxidization of L-ascorbic acid. Under light microscopy, the crystals had the shape of needles, or small diamonds (approx. 10–50 μm in length).

The in vitro tests were conducted using two types of human skin. A full thickness of human forearm cadaver skin (52-year-old man) obtained from The National Disease Research Interchange (Philadelphia, Pa.) and fresh human skin received immediately after plastic surgery (The Research Institute for Plastic, Cosmetic and Reconstructive Surgery, Inc.) The fresh skin samples were from the neck and face of both males and females. Full thickness skin was prepared for use in the experiments by trimming away the fat under the dermis. The thickness was 1.2 mm for female neck skin and 1.8 mm for skin from other locations.

Experimental setup

In order to control the environment for human cosmetic applications, a custom-made glove box was constructed for the study of clear plastic with dimensions of 60 cm×40 cm×30 cm. The glove box was fitted with a light bulb, an electrical fan, a heater, a humidity controller (set at 40% humidity), and a thermostat (set at 35°±1° C.). The diameter of the glove hold was about 21 cm. The top of the box could be removed to transport experimental items, but the box was sealed during operation. Temperature was determined to be steady prior to the experiments. Two outputs from a pulse generator were connected to electrodes through a wall opening in the box.

An exponential pulse generator (Model ECM600, BTX, a Division of Genetronics Inc., San Diego, Calif.) connected to meander electrodes (Model P/N 454-P, Genetronics Inc.) were used for all experiments. The area of electrode exposed to the skin during pulsing was 1–1.5 cm$^2$, varying with the size of skin samples. The skin was placed on a brass metal plate during the pulsing, with the meander electrode located on top of the stratum corneum. The metal plate was used as a substitute for conductive underlying tissue for the in vitro study. Skin resistance was measured prior to the experimental process. It was 100–150 kohms and 300–800 kohms for cadaver and fresh surgical skin, respectively. The protocol for electroporation of the cadaver skin was as follows: 100 V for 20 msec, 6 pulses with 15 sec time intervals between pulses. For fresh skin, the protocol was: 60 V for 30 msec, 6 pulses for cream; 60 V for 2.7 msec and 5 msec, 6 pulses for the suspension (with 2.5 sec time interval between pulses to shorten the time of the treatment and reduce the loss of L-ascorbic acid).

For a control, the conventional cosmetic procedure for cosmetic skin resurfacing of humans in physicians' offices was simulated. The conventional procedure involves applying Intaglio® cream on facial skin, placing a finger on the skin surface, and making a few circles clockwise and counter clockwise. In the simulated control procedure, a force (300 g) from a calibrated spring-loaded plastic cylinder was applied to the surface of the skin samples through the meander electrode. The pressure was held constant during pulsing at 200 g cm$^{-2}$. Then, the cylinder was moved gently 6 times clockwise and counter clockwise, maintaining pressure for a total of 30 sec.

A further control studied the natural absorption of L-ascorbic acid suspension on the skin (with no pressure and massage and no pulsing).

The final step for each of the test and control groups was washing the L-ascorbic acid-containing composition from the surface of the skin samples quickly and gently. The skin surface was wiped with cotton Q-tips 4 times in the following sequence: wet-dry-wet-dry. Then the skin sample was immediately placed in a dry petri dish with the stratum corneum on the bottom, the skin was cut from dermis to stratum corneum into two parts, each piece was put in a small centrifuge tube, and left on dry ice for the HPLC assay to determine the concentration of the L-ascorbic acid that penetrated into each skin sample.

HPLC analysis

Each frozen sample was weighed and 300 μl of extraction solution (0.1% methylprogesterone acetate (MPA), 0.1 mM EDTA) were added to each sample. Each sample was homogenized for one minute with a tissue grinder. The tip of the grinder was rinsed with 500 μl of extraction solution, and the final volume was brought to 1 ml with extraction solution. Appropriate sample dilutions were prepared with the extraction solution.

Electrochemical HPLC was performed to determine the amount of L-ascorbic acid per gram of skin using an ion exclusion column (BioRad Laboratories, Richmond, Calif.) at 30° C. The mobil phase was 0.001 M $H_2SO_4$ with a flow rate of 0.6 ml min$^{-1}$. The injection volume was 10 μl. An ESA Coulochem Detector was used with settings at 0.4 V, gain 10×x1. The retention time was 10.0 min. Standard curves were prepared for L-ascorbic acid concentrations of 1, 2, 5, 10, and 30 μg L$^{-1}$.

The results of these experiments show that for the cream formulation (pH 3.5) electroporation enhanced penetration of L-ascorbic acid by 38% (see Table 1 below); whereas for the suspension formulation (pH 1.86) there was no significant improvement of L-ascorbic acid penetration attributable to electroporation. The control group (pressure and massage, but no pulsing) showed the effect of pushing the L-ascorbic acid-containing composition into the skin.

TABLE 1

Results from human cadaver skin

| Formulation (% of L-ascorbic acid (Asc) | Asc in the skin (mg g$^{-1}$ of skin) | |
| --- | --- | --- |
| | No Pulsing | Pulsing |
| Cream (20%) | 0.47 ± 0.18 | 0.65 ± 0.43 |
| Suspension (w/v: 33%) | 5.65 ± 3.68 | 6.03 ± 2.24 |

100 V, 20 ms, 6 pulses, n = 3–5

By contrast, the natural absorption of L-ascorbic acid suspension on the skin (with no pressure and massage and no pulsing) was measured after the same washing steps (see Table 2). The comparatively high absorption of the suspension may be due to the lower pH of this composition (pH 1.86).

TABLE 2

Results from basic controls by HPLC

| Skin source (background of Asc) | HPLC test (Asc mg g$^{-1}$ of skin) |
| --- | --- |
| Cadaver skin | 0.01 |
| Fresh surgical skin  Female's facial skin | 0.01 |
| Male's facial skin | 0.02 |
| Passive absorption of Asc in the cadaver skin (suspension 33%) | 0.11 |

| Labeled Vitamin C sample | HPLC test |
| --- | --- |
| Suspension (28% and 33%) | 28.5% and 36.8% |
| Cream (20%) | 19.7% |
| Sigma Vitamin C (5 µg ml$^{-1}$) | 4.95 µg ml$^{-1}$ |

For the fresh surgical skin model, the results of electroporation-mediated topical delivery of L-ascorbic acid (Table 3) show that L-ascorbic acid penetration was increased 300% compared to the control with the cream formulation, and there was approximately a 54% increase for the suspension formulation.

TABLE 3

Results from human fresh surgical skin

| Formulation (% of Asc) | Asc (mg g$^{-1}$ of skin) | | | |
| --- | --- | --- | --- | --- |
| | No pulsing | | Pulsing | |
| Cream (20%) | 0.075 ± 0.007 | | 30 ms | 0.22 ± 0.12 |
| Suspension (w/v: 33%) | 2.600 ± 0.70 | | 2.7 ms | 3.05 ± 1.00 |
| | | | 5 ms | 4.01 ± 0.90 |

60 V, 6 pulses; n = 2 (cream), n = 3–5 (suspension)

This result may be attributed, in part, to the lower pH of the suspension formulation and to the lower test voltage and shorter pulse length used with the suspension formulation, which was selected as a result of human tolerance information provided from the human volunteer test described herein in Example 3 below.

Surprisingly, the results (Table 3) of the basic control studies show that passive absorption of L-ascorbic acid in the cadaver skin samples for the 33% suspension was an order of magnitude higher than for the fresh surgical skin samples.

EXAMPLE 3

To obtain the tolerability of electrical sensation with reference to the pulsing parameters, such as voltage and pulse length, a pilot human volunteer was tested. It was expected that the nerve sensation would be related to three variables, or a combination thereof: (i) pulse parameters, (ii) the L-ascorbic acid formulation (i.e., whether cream or suspension) and (iii) location of the skin site. Not surprisingly, the facial skin was found to be more sensitive than the forearm skin during the electroporation. On the facial skin, the tolerance threshold pulse parameters for a single pulse turned out to be 80 V and 20 msec (for the test cream), and 50 V and 2 msec (for the test suspensions). On the forearm, higher tolerance (for the test suspensions) was observed at 70V and 10 msec.

While the invention has been described in detail with reference to certain preferred embodiments thereof, it will be understood that modifications and variations are within the spirit and scope of that which is described and claimed.

What is claimed is:

1. A method for treating degenerative skin conditions in a subject in need thereof, said method comprising applying at least one electric pulse to the surface of a region of skin and applying thereto a composition comprising L-ascorbic acid, or a cosmetically/pharmaceutically acceptable salt, ester or other derivative thereof, said electric pulse having a voltage from about 25 volts to about 120 volts and sufficient duration to cause electroporation of said region of skin, thereby delivering an effective amount of the L-ascorbic acid or the derivative thereof through the stratum corneum of the region of skin so as to improve the condition of the region of skin without substantial pain or skin irritation.

2. The method according to claim 1 whereby production of collagen is enhanced in the region of skin.

3. The method according to claim 1 wherein the level of free oxygen radicals is reduced in the region of skin.

4. The method according to claim 1 wherein the concentration of L-ascorbic acid, or the derivative thereof, in the composition is in the range from about 1% to about 35% by volume.

5. The method according to claim 1 wherein the composition is formulated as a cream, spray or lotion.

6. The method according to claim 1 wherein the composition is formulated as an emulsion, a crystal suspension, or the L-ascorbic acid, or the derivative thereof, is encapsulated in liposomes or microspheres.

7. The method according to claim 1 wherein the composition is formulated as an aqueous solution or suspension.

8. The method according to claim 1 wherein the electrical pulse is monopolar or bipolar.

9. The method according to claim 1 further comprising iontophoresis.

10. The method according to claim 1 wherein the electric pulse has a voltage from about 50 volts to about 80 volts.

11. The method according to claim 1 wherein a plurality of the electric pulses are applied.

12. The method according to claim 11 wherein the plurality of pulses comprises at least one train of from about 1 to about 30 pulses.

13. The method according to claim 12 wherein a plurality of the trains is applied.

14. The method according to claim 11 wherein the time interval between the plurality of pulses is in the range from about 0.1 sec to about 15 sec.

15. The method according to claim 1 wherein the pulse duration is in the range from about 10 lsec to about 100 msec.

16. The method according to claim 15 wherein the pulse duration is in the range from about 500 µsec to about 50 msec.

17. The method according to claim 15 wherein the pulse duration is in the range from about 2.0 msec to about 20 msec.

18. The method according to claim 1 wherein the region of skin is on the face, hand, arm, neck, chest, or leg, and the composition is formulated as a cream or lotion.

19. The method according to claim 18 wherein the electric pulse has a voltage from about 60 volts to about 80 volts and a duration in the range from about 2.7 msec to about 20 msec.

20. The method according to claim 1 wherein the region of skin is on the face, hand, arm, neck, chest, or leg and the composition is formulated as an aqueous suspension or solution.

21. The method according to claim 20 wherein the electric pulse has a voltage up to about 50 volts and a duration of up to 2 msec.

22. The method according to claim 1 wherein the pH of the composition is in the range from about 1.85 to about 5.0 and delivery of the L-ascorbic acid, or the derivative thereof, is enhanced as compared with passive delivery thereof.

23. The method according to claim 1 wherein the derivative is L-ascorbic acid -2-phosphate or magnesium ascorbyl phosphate.

24. The method according to claim 1 wherein the pH of the composition is in the range from about 1.85 to about 3.9 and the and delivery of the L-ascorbic acid, or the derivative thereof, is enhanced as compared with passive delivery thereof.

25. The method according to claim 1 further comprising chemically or mechanically enhancing the permeability of the stratum corneum.

26. The method according to claim 25 wherein the enhancing involves application to the region of skin of a chemical enhancer or microdermalabrasion.

27. A method for electroporation-enhanced dermatological delivery of L-ascorbic acid through the stratum corneum of a subject in need thereof, said method comprising applying at least one electric pulse to the surface of a region of skin so as to cause electroporation of the region of skin and applying thereto a composition comprising ascorbic acid, or a cosmetically/pharmaceutically acceptable salt, ester or other derivative thereof, said electric pulse having a voltage from about 25 volts to about 120 volts and sufficient duration to topically deliver an effective amount of the L-ascorbic acid or the derivative to the region of skin.

28. The method according to claim 27 further comprising iontophoresis.

29. A method according to claim 27 wherein the delivery is without substantial pain or skin irritation.

30. The method according to claim 27 wherein the concentration of L-ascorbic acid or the derivative thereof in the composition is in the range from about 20% to about 33% by volume.

31. The method according to claim 28 wherein the composition is formulated as a cream, spray or lotion.

32. The method according to claim 27 wherein the composition is formulated as an emulsion, a crystal suspension, or the L-ascorbic acid or the derivative is encapsulated in liposomes or microspheres.

33. The method according to claim 27 wherein the composition is formulated as an aqueous solution or suspension.

34. The method according to claim 27 wherein the electrical pulse is monopolar or bipolar.

35. The method according to claim 27 wherein the topical delivery reduces the level of free oxygen radicals in the region of skin.

36. The method according to claim 27 wherein the electric pulse has a voltage from about 50 volts to about 80 volts.

37. The method according to claim 27 wherein a plurality of the electric pulses are applied.

38. The method according to claim 37 wherein the plurality of pulses comprises at least one train of from about 1 to about 10 pulses.

39. The method according to claim 38 wherein a plurality of the trains is applied.

40. The method according to claim 38 wherein the time interval between the plurality of pulses is in the range from about 0.1 sec to about 15 sec.

41. The method according to claim 27 wherein the pulse duration is in the range from about 100 $\mu$sec to about 100 msec.

42. The method according to claim 41 wherein the pulse duration is in the range from about 500 $\mu$sec to about 50 msec.

43. The method according to claim 27 wherein the pulse duration is in the range from about 2.0 msec to about 20 msec.

44. The method according to claim 27 wherein the region of skin is on the face hand, arm, neck, chest, or leg, and the composition is formulated as a cream or lotion.

45. The method according to claim 44 wherein the electric pulse has a voltage of about 60 volts to about 80 volts and a duration in the range from about 2.7 msec to about 20 msec.

46. The method according to claim 27 wherein the region of skin is on the face, hand, arm, neck, chest, or leg and the composition is formulated as an aqueous suspension or solution.

47. The method according to claim 46 wherein the electric pulse has a voltage up to about 50 volts and a duration of up to 2 msec.

48. The method according to claim 28 wherein the pH of the composition is in the range from about 4.0 to about 5.0 and delivery of the L-ascorbic acid or the derivative thereof is enhanced as compared with passive delivery thereof.

49. The method according to claim 28 wherein the derivative is L-ascorbic acid -2-phosphate or magnesium ascorbyl phosphate.

50. The method according to claim 28 wherein the pH of the composition is in the range from about 1.85 to about 3.9 and the topical delivery of the L-ascorbic acid or the derivative thereof is enhanced as compared with passive delivery thereof.

51. The method according to claim 27 further comprising iontophoresis.

52. The method according to claim 27 wherein the topical delivery enhances production of collagen in the region of skin.

53. The method according to claim 27 further comprising chemically or mechanically enhancing the permeability of the stratum corneum.

54. The method according to claim 53 wherein the enhancing involves application to the region of skin of a chemical enhancer or microdermalabrasion.

* * * * *